(12) United States Patent
Stauffer

(10) Patent No.: US 8,273,927 B2
(45) Date of Patent: Sep. 25, 2012

(54) ALCOHOL FRACTIONATION

(76) Inventor: John E. Stauffer, Greenwich, CT (US)

( * ) Notice: Subject to any disclaimer, the term of this patent is extended or adjusted under 35 U.S.C. 154(b) by 205 days.

(21) Appl. No.: 12/858,566

(22) Filed: Aug. 18, 2010

(65) Prior Publication Data

US 2012/0046504 A1 Feb. 23, 2012

(51) Int. Cl.
*C07C 29/74* (2006.01)
(52) U.S. Cl. ........ 568/916; 568/918; 568/919; 568/920; 568/921
(58) Field of Classification Search .......... 568/918–921, 568/916
See application file for complete search history.

(56) References Cited

U.S. PATENT DOCUMENTS

| | | | | |
|---|---|---|---|---|
| 1,452,206 A | * | 4/1923 | Mann, Jr. | 568/916 |
| 2,668,863 A | * | 2/1954 | Norris | 203/34 |
| 2,949,427 A | * | 8/1960 | Andersen et al. | 516/135 |
| 3,689,371 A | * | 9/1972 | Kerber et al. | 203/37 |
| 4,454,359 A | * | 6/1984 | Colgrove et al. | 568/916 |
| 4,594,466 A | * | 6/1986 | Reeves | 568/919 |
| 4,743,707 A | * | 5/1988 | Matsuhira | 568/919 |

* cited by examiner

*Primary Examiner* — Brian J Davis
(74) *Attorney, Agent, or Firm* — Young Basile Hanlon & MacFarlane PC

(57) ABSTRACT

A process is provided for the recovery of alcohol from its aqueous solution by dissolving caustic in the solution to generate a phase separation. One layer contains the alcohol product and the other layer waste water. By recovering and recycling the caustic, a self-contained process is realized.

1 Claim, 1 Drawing Sheet

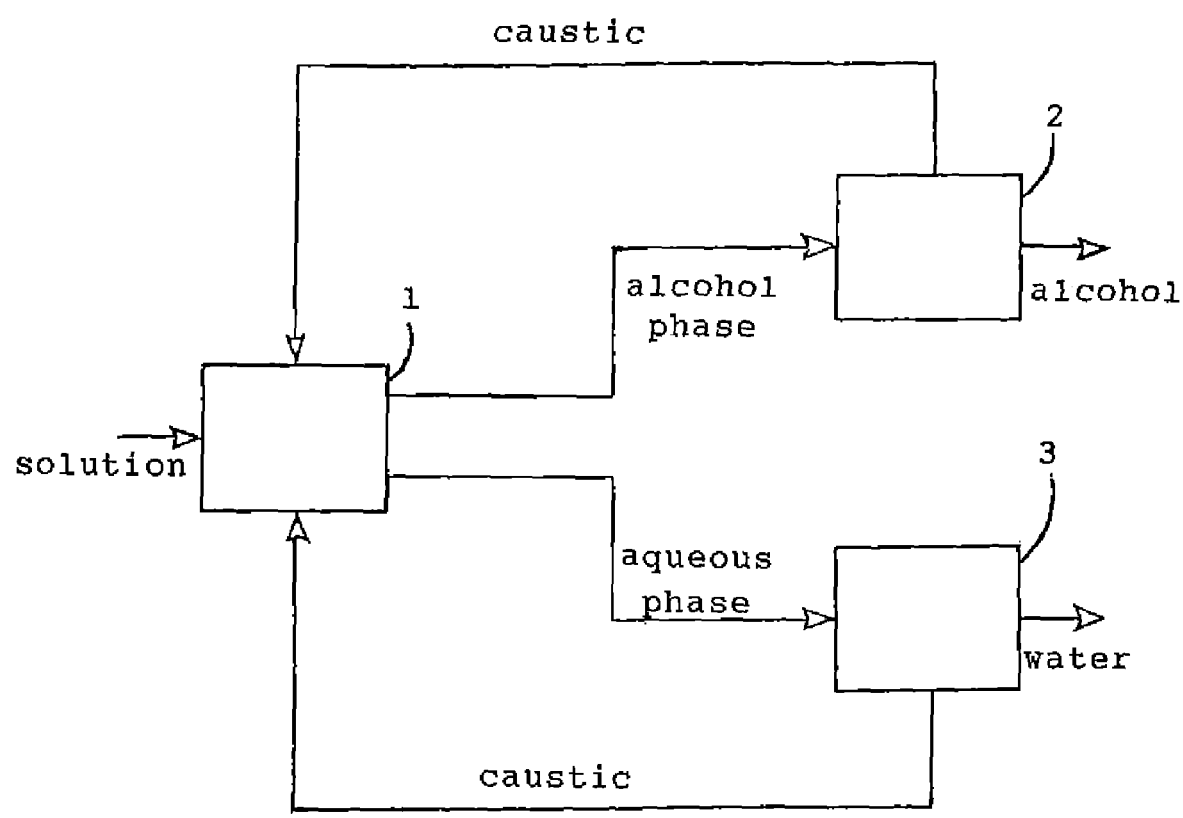

ALCOHOL FRACTIONATION

FIELD OF THE INVENTION

This invention relates to a process for the partition of an aqueous alcohol solution into two fractions, an alcohol phase and a water phase. In the process, an alkali metal hydroxide is added to the aqueous alcohol solution, thus causing the solution to undergo a phase separation. The resulting phases are evaporated to recover the alkali metal hydroxide, which is recycled in the process.

BACKGROUND OF THE INVENTION

Many processes for the manufacture of alcohols produce an intermediate stream comprising an aqueous alcohol solution. This solution must be fractionated in order to produce the final alcohol product.

The accepted practice for the fractionation of alcohol solutions is to use distillation. While effective in this application, distillation has several drawbacks. A primary disadvantage of distillation is that it consumes considerable amounts of energy. Thus, as much as 50 to 80 percent of the energy required to produce ethanol in a typical fermentation process is consumed in the distillation step.

An added problem in producing absolute alcohol is that an azeotrope or constant boiling solution is formed during distillation. Ethanol, for example, produces an azeotropic composition of 95 weight percent alcohol and the balance water. Isopropyl alcohol has a binary azeotrope of 91 weight percent alcohol, the rest being water.

To circumvent the limitations posed by azeotropes, several creative procedures have been used. The classic method of producing anhydrous ethanol is to use benzene to break the azeotrope. This approach, however, introduces a toxic impurity. A newer technique is to resort to the use of molecular sieves to dehydrate the alcohol.

SUMMARY OF THE INVENTION

It is an object of the present invention to provide a process for the fractionation of alcohol that is energy efficient, easy to apply, and adaptable to the production of large quantities of alcohol. This and other objects, features and advantages of the present invention will become apparent from the following description and the FIGURE that is included.

A process is provided for the fractionation of alcohol from aqueous solutions of alcohol. In the process, caustic comprising an alkali metal hydroxide is added to the solution to produce a phase separation. In this manner, water is separated from the alcohol. The resulting two streams are evaporated in order to recover the caustic, which can be recycled to the addition step.

The alkali metal hydroxide includes the hydroxides of any alkali metal. Thus, sodium hydroxide as well as potassium hydroxide are eminently suitable. The solubilities of these hydroxides govern the level of their addition.

The process of the present invention has general applicability. For example, it can be used to produce ethanol of any concentration. It can also be applied to the manufacture of isopropyl alcohol. Additionally, the process is applicable to butyl alcohol synthesis.

Other applications of the present invention will become apparent to those skilled in the art when the following description of the best mode contemplated for practicing the invention is read in conjunction with the accompanying drawings.

BRIEF SUMMARY OF THE DRAWINGS

The description herein makes reference to the accompanying drawings wherein like reference numerals refer to like parts throughout the several views and wherein:

FIG. 1 is a block diagram showing the principal steps of the process, including the addition of hydroxide to the alcohol solution and the recovery of the hydroxide.

DETAILED DESCRIPTION OF THE ILLUSTRATIVE EMBODIMENT

The process of the present invention can be conducted either as a batch operation or as a continuous process. In the batch mode of operation, an alkali metal hydroxide is added to a tank 1 containing an aqueous alcohol solution. For example, flaked sodium hydroxide can be introduced in to a tank of 20% ethanol. Alternatively 73% caustic soda can be used. Mixing is provided by any effective means of agitation. Cooling coils or tank jacketing are preferably used to remove the heat of solution. Given the corrosive nature of caustic, the equipment is best fabricated from suitable alloys.

Upon addition of the alkali metal hydroxide, a phase separation occurs almost immediately. The top layer contains alcohol and the bottom layer water. The alcohol phase is decanted while the aqueous phase is drained from the bottom of the tank. Even though the interface is clearly defined, careful control over the separation should be followed.

Each of the streams from the mixing tank is sent to a separate evaporator 2 or 3 to remove the dissolved caustic. In this manner, an alcohol product is obtained while a waste aqueous stream is produced. Depending on product specifications, additional treatment may be required to manufacture the finished product. The evaporators 2, 3 used are of standard design. Energy efficiency and investment cost are of prime consideration.

The present invention can better be visualized by referring to the schematic flow sheet of FIG. 1. In this diagram, mixing tank 1 receives the alcohol solution and caustic additive. Evaporator 2 separates the alcohol product from the dissolved caustic. By recycling the caustic streams, a self-contained process is achieved.

EXAMPLES

1. In this experiment, 40.3 gm. of sodium hydroxide ACS crystals was dissolved in 200 ml. 80 proof vodka containing 40% ethyl alcohol by volume. Three drops of green food color containing FD&C Yellow 5 and FD&C Blue 1 was added. The warm solution separated into two phases; a top layer brightly colored red and a bottom layer that was clear yellow. The total volume of both phases was 204 ml. and the interface was at 96 ml. When a sample of the top layer was lit, it burned vigorously.
2. Similarly to example 1, 71.1 gm. of sodium hydroxide was dissolved in 100 ml. water and 100 ml. 80 proof vodka. A phase separation occurred, the aqueous phase equaling 180 ml. and the alcohol phase having a volume of 29 ml.
3. Instead of ethanol, isopropyl alcohol was used in this run. A total of 56.8 gm. of sodium hydroxide was added to approximately 200 ml. of 70% rubbing alcohol comprising isopropyl alcohol and water. Not all of the caustic was dissolved, but a phase separation immediately formed. The top layer of alcohol equaled 146 ml. and the bottom aqueous layer totaled 64 ml.
4. Finally, 155.2 gm. of potassium hydroxide was dissolved in 200 ml. of 80 proof vodka. A distinct phase separation was observed. The total volume of both phases was close to 262 ml. and the interface was at 165 ml.

What is claimed is:

1. A continuous process for the recovery of alcohol from an aqueous solution of the alcohol comprising the steps of:
    adding caustic to the solution to cause the partition of the solution into an alcohol rich phase and an aqueous phase;
    separating the two phases;
    recovering alcohol from the alcohol rich phase by evaporation;
    removing water from the aqueous phase by evaporation; and
    recycling streams of dissolved caustic from each of the evaporation steps to the addition step.

* * * * *